United States Patent
Sato et al.

(10) Patent No.: US 6,750,336 B2
(45) Date of Patent: Jun. 15, 2004

(54) METHOD OF PRODUCTION OF LACTAM

(75) Inventors: Osamu Sato, Miyagi (JP); Kiyotaka Hatakeda, Miyagi (JP); Yutaka Ikushima, Miyagi (JP); Kazuo Torii, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/285,571

(22) Filed: Nov. 1, 2002

(65) Prior Publication Data

US 2003/0088093 A1 May 8, 2003

(30) Foreign Application Priority Data

Nov. 2, 2001 (JP) .......................... 2001-338121

(51) Int. Cl.$^7$ ............................................. C07D 201/04
(52) U.S. Cl. ..................................... 540/535; 540/536
(58) Field of Search .................................. 540/535, 536

(56) References Cited

U.S. PATENT DOCUMENTS 6,300,523 B1   10/2001   Ikushima et al. ............ 568/383

FOREIGN PATENT DOCUMENTS

JP          10-287644          10/1998

OTHER PUBLICATIONS

Osamu Sato, et al. "Noncatalytic Beckmann Rearrangement of Cyclohexanone–Oxime in Supercritical Water" The Journal of Organic Chemistry, vol. 63, No. 24, 1998, pp. 9100–9102.

Yutaka Ikushima, et al. "Acceleration of Synthetic Organic Reactions Using Supercritical Water: Noncatalytic Beckmann and Pinacol Rearrangements" Journal of the Amerciain Chemical Society, vol. 122, No. 9, 2000, pp. 1908–1918.

Yutaka Ikushima, et al. "Noncatalytic Organic Synthesis Using Supercritical Water: The Peculiarity Near the Critical Point" Angewandte Chemie, 38, No. 19, 1999, pp. 2910–2913.

*Primary Examiner*—Bruck Kifle
(74) *Attorney, Agent, or Firm*—Oblon, Spivak, McClelland, Maier & Neustadt, P.C.

(57) ABSTRACT

A method for producing a lactam by using an organic solvent as a substrate solution, which makes it possible to introduce a high-concentration oxime into flowing high-temperature and high-pressure water, thereby allowing the high-concentration lactam to be synthesized with a high efficiency. With this method, the lactam is continuously synthesized at a high rate from the oxime under high-temperature and high-pressure water mixture conditions within a temperature range of no less than 250° C. and a pressure range of no less than 15 MPa.

9 Claims, 1 Drawing Sheet

Fig. 1

METHOD OF PRODUCTION OF LACTAM

BACKGROUND OF THE INVENTION

1. Field of the Invention

The present invention relates to a method for continuously producing lactams from oximes under high-temperature and high-pressure conditions, and more particularly to a novel method for continuously producing lactams by which lactams are continuously produced by conducting a rearrangement reaction of oximes dissolved in an organic solvent under high-temperature and high-pressure water mixture conditions. The present invention makes it possible to produce lactams by a method requiring no neutralization of a large quantity of spent sulfuric acid, as required in the conventional methods for producing lactams which use concentrated sulfuric acid as a catalyst.

2. Description of the Related Art

In industrial production of lactams, for example, $\epsilon$-caprolactam employed as a starting material for Nylon 6, the lactams have been produced by a Beckman rearrangement reaction method from oximes of carbonyl compounds such as cyclohexanone oxime. The rearrangement reaction uses an acid catalyst, and because the acid boils during the reaction, the presence of water, though in a very small quantity, causes hydrolysis of oximes, thereby decreasing the yield of lactams. In order to prevent this decrease, a method is typically employed in which fuming sulfuring acid is used as an acid catalyst and the acid boils during the reaction. With such a method, the reaction is conducted under severe conditions and is known to create problems in terms of corrosion of equipment materials, danger of the production process, and treatment of ammonium sulfate which is a byproduct. Sulfuric acid used during lactam recovery had to be neutralized with ammonia, producing ammonium sulfate as a byproduct at no less than 2 kg per 1 kg of lactam. Because ammonium sulfate is of a low industrial value, it is difficult to use and has to be treated.

In recent years, the development of simple and effective chemical processes in which the reaction is completed within a short time and which use no hazardous substances, such as fuming sulfuric acid, has been pursued in the field of chemical industry against the background of growing concerns about the degradation of global environment. In the production of lactams, a demand has been created for the development of effective new production processes which use no fuming sulfuric acid that creates problems in terms of corrosion of equipment materials, operational safety, and environmental pollution and in which no byproducts are produced.

The following two methods have been suggested to resolve those problems, both methods employing reaction under high-temperature and high-pressure water and using absolutely no high-concentration strong acid catalysts such as fuming sulfuric acid and the like: (A) batch synthesis method (O. Sato, Y. Ikushima and T. Yokoyama, Journal of Organic Chemistry 1998, 63, 9100–9102) and (B) flow synthesis method (Y. Ikushima, K. Hatakeda, O. Sato, T. Yokoyama and M. Arai, Journal of American Chemical Society 2000, 122, 1908–1918).

With the batch synthesis method (A), cyclohexanone oxime is sealed in a stainless steel tube with an inner capacity of 10 mL, the tube is placed in a salt bath, the temperature is raised to 200 to 400° C. within a time of about 30 seconds, and the product is obtained by conducting the reaction for 3 minutes. This method apparently was not designed for large-scale industrial production, but attracted attention as a synthesis method using no acid catalyst such as fuming sulfuric acid and the like. Because with this method the reaction is completed in a single cycle, the operations are intermittent and a time of about 20 to 30 seconds is required to raise the temperature to a set temperature. Therefore, the drawback is that a large quantity of cyclohexanone which is a hydrolyzate is formed when the temperature is raised, and the yield of the target $\epsilon$-caprolactam is decreased. Furthermore, because cyclohexanone is a starting material for cyclohexanone oxime, a reverse reaction is initiated in this method and the method can be considered as a deathblow to the industrial process.

(B) With the flow synthesis method, the operation is continuous which is apparently advantageous for mass production, but because an aqueous solution of cyclohexanone oxime at room temperature is heated and used as a high-temperature and high-pressure carrier, a certain time is apparently required to raise the temperature to a set reaction temperature. The results obtained in the experiment in which the substrate was caused to react for 113 seconds under the conditions of 350° C. and 22.1 MPa, showed that only cyclohexanone was obtained as a product and absolutely no $\epsilon$-caprolactam was obtained. Furthermore, the results indicated that even under a temperature condition of 374.5° C., both $\epsilon$-caprolactam and cyclohexanone were formed. Therefore, the drawback of this method is that time is required to raise the temperature, similarly to the batch synthesis method (A) and, for example, while water serving as a solvent is in a hydrothermal state at 100 to 300° C., hydrolysis of cyclohexanone oxime proceeds resulting in the formation of cyclohexanone and decrease in the yield of target $\epsilon$-caprolactam. Another drawback of this method is that cyclohexanone oxime has poor solubility in water. Therefore, the method was suitable only for reactions with low-concentration substrates, was ineffective, and required improvement.

With the above-described prior art technology in view and against the aforesaid background, the inventors have conducted a comprehensive study of methods for producing lactams from oximes at a high temperature and under a high pressure. In the course of the study, the inventors have discovered that increasing the temperature of high-concentration oximes to a set reaction temperature within a short time is important for continuous and effective manufacture of lactams from oximes under high-temperature and high-pressure conditions. The research was further advanced based on this finding and eventually brought the present invention to completion.

SUMMARY OF THE INVENTION

Thus, the production method in accordance with the present invention that has been developed by the inventors via a variety of experiments is, for example, a method for producing caprolactam selectively, effectively, and within a short time, while suppressing hydrolysis of an oxime, by directly and continuously introducing an organic solvent having the oxime dissolved therein into a reaction field under high-temperature and high-pressure water conditions and attaining a set reaction temperature within a short time.

It is an object of the present invention to provide a method for selectively producing large quantities of lactams without the formation of cyclohexanone, by introducing an oxime dissolved into an organic solvent in high-temperature and high-pressure water and conducting a reaction of the high-concentration substrate with the reduced temperature increase time.

The present invention that resolves the above-described problems comprises the following technological means.

DESCRIPTION OF THE PREFERRED EMBODIMENTS

The present invention will be described hereinbelow in greater detail.

To facilitate the explanation of the present invention, it will be described in detail with reference to a process in which an acetonitrile solution containing an oxime dissolved therein is introduced into high-temperature and high-pressure water, the reaction temperature is attained within a short time of no more than 3 seconds, and a lactam is produced under a reaction pressure condition of 40 MPa.

The production method in accordance with the present invention that has been developed by the inventors via a variety of experiments is, for example, a method for synthesizing ε-caprolactam by the rearrangement reaction of cyclohexanone oxime, without a hydrolysis reaction, by continuously introducing an acetonitrile solution having cyclohexanone oxime dissolved therein into a reaction field under flowing high-temperature and high-pressure water conditions and attaining a set reaction temperature of, for example, 375° C. within a short time of no more than 3 seconds. In accordance with the present invention, because high-temperature and high-pressure water is used as a reaction field or reaction solvent, large quantities of wastes such as spent catalysts or ammonium sulfate, which have to be treated, are not discharged. Furthermore, cyclohexanone, which is the product of cyclohexanone oxime hydrolysis, is not scarcely generated. The unreacted supplied starting materials can be reused for the reaction in accordance with the present invention. Furthermore, because the method in accordance with the present invention can use a high-concentration substrate starting material dissolved in an organic solvent and a high-concentration product can be continuously produced at a high rate and a good yield, this method is apparently most advantageous as means for producing lactams.

A method for producing lactams in accordance with the present invention will be described below.

In accordance with the present invention, a set reaction temperature is attained within a short time, hydrolysis of an oxime is suppressed, and a high-concentration lactam can be selectively and effectively produced within a short reaction time, for example, by continuously introducing an organic solvent having the oxime dissolved therein into a reaction field under high-temperature and high-pressure water conditions.

In accordance with the present invention, an oxime used as a substrate starting material is represented by the general formula 1 hereinbelow, where n=1 to 9 and $R_1$ is H or alkyl group. Any alkyl group containing 1 to 20 carbon atoms, such as methyl group, ethyl group, propyl group, butyl group, and the like, can be used as the alkyl group. Cyclohexanone oxime can be presented as an example of oximes, but the present invention is not limited to cyclohexanone oxime.

[Formula 1]

$$H_2C\text{------}C=NOR_1$$
$$|\quad\quad\quad\quad|$$
$$(CH_2)n\text{------}CH_2$$

The lactam obtained in accordance with the present invention is represented by the general formula 2 hereinbelow, where n=1 to 9 and $R_1$ is H or alkyl group. Any alkyl group containing 1 to 20 carbon atoms, such as methyl group, ethyl group, propyl group, butyl group, and the like, can be used as the alkyl group.

[Formula 2]

The lactams obtained in accordance with the present invention are multimembered ring lactams with rings consisting of no less than five members, for example, five-membered ring lactams, six-membered ring lactams, seven-membered ring lactams, and the like. Examples include, ε-caprolactam, γ-butyrolactam, γ-valerolactam, δ-valerolactam, and the like; the present invention is, however, not limited to those examples.

As a specific example of producing lactams in accordance with the present invention, the general formula 3 hereinbelow represents a reaction formula of ε-caprolactam formation from cyclohexanone oxime, this reaction relating to an example of producing a seven-membered ring lactam.

[Formual 3]

cyclohexanone oxime      ε – caprolactam

Synthesis of lactams by Beckman rearrangement reaction of oximes is known to proceed in the presence of an acid catalyst. It is a very interesting fact that in accordance with the present invention lactams are synthesized by Beckman rearrangement reaction from oximes dissolved in an organic solvent under high-temperature and high-pressure conditions. It may be guessed that in high-temperature and high-pressure water the acid catalyst function can be demonstrated because of proton generation or polarization of water molecule structure, but whether the organic solvent used in accordance with the present invention functions as a catalyst is yet to be verified by further advancing physico-chemical research relating to high-temperature and high-pressure water.

In accordance with the present invention, an oxime which is a substrate dissolved in an organic solvent is set to the prescribed high-temperature and high-pressure conditions within a short time. As a result, the hydrolysis reaction can be suppressed and a lactam can be produced selectively. Furthermore, a small amount of amino acids is formed in this reaction. For example, when ε-caprolactam was synthesized from cyclohexanone oxime dissolved in acetonitrile by conducting the reaction for 0.659 second under high-temperature and high-pressure conditions of a temperature of 375° C. and a pressure of 40 MPa, the yield of ε-caprolactam was 80.5%, whereas the yield of 6-aminohexanoic acid was 5.2%. 6-Aminohexanoic acid is important as a starting material monomer for producing polycaprolactam and can be comparatively easily converted into ε-caprolactam, this reaction also proceeding in high-temperature and high-pressure water. In this reaction, cyclohexanone which is a hydrolysis product of cyclohexanone oxime has not scarcely been detected.

In accordance with the present invention, ε-caprolactam can be obtained by preparing a substrate solution in which an oxime as a starting material substrate is dissolved in an organic solvent and conducting the reaction under a high temperature and high pressure. The reaction, however, proceeds even more effectively if an acid is present in the reaction system. Either mineral acids or organic acids can be used in accordance with the present invention. Examples of suitable mineral acids include sulfuric acid, hydrochloric acid, nitric acid, perchloric acid, carbonic acid, and the like. Examples of suitable organic acids include acetic acid, oxalic acid, lactic acid, tartaric acid, and the like. Those acids can be used as a catalyst individually or as a mixture of two or more thereof. The acid used for the reaction can be introduced together with the oxime, which is a reaction substrate, or separately therefrom into high-temperature and high-pressure water by using a water pump. The acid can be also used by admixing it in advance to carrier water.

The concentration of the acid used changes according to the initial temperature of carrier water, reaction pressure, flow velocity of carrier water, inlet flow velocity of oxime or aqueous solution thereof, quantity of introduced oxime, type of the reaction, capacity of the reactor, and the like, and can be adjusted. Generally, the acid concentration can advantageously be selected within a concentration range of 0.001 mM–10 M. The acid concentration can be more advantageously selected within a range of 0.01 mM–5 M. The acid concentration can be even more advantageously selected within a range of 0.01 mM–3 M. The acid concentration can be most advantageously selected within a range of 0.01 mM–1 M.

In accordance with the present invention, distilled water, ion-exchange water, tap water, underground water, and the like can advantageously be used as a starting material for high-temperature and high-pressure water. When water of the above-mentioned types is used as a starting material for high-temperature and high-pressure water, dissolved oxygen can cause oxidation and decomposition of organic substances in case the water is used as high-temperature and high-pressure water, in particular, supercritical water. Therefore, it is desirable that the dissolved oxygen be removed in advance by bubbling with nitrogen gas or the like. When high-temperature and high-pressure water is used in a subcritical state, it is not that necessary to remove dissolved oxygen from the starting material water, but the oxygen still may be removed.

The temperature of high-temperature and high-pressure water used in accordance with the present invention can be controlled by using a molten salt or heater from the outside of the reactor. Alternatively, the temperature can be controlled by an internal heating system inside the reactor. Furthermore, the high-temperature and high-pressure water can be prepared in advance and supplied into the reactor from the outside with a water pump or the like to conduct the reaction. The reaction conditions can be also controlled by supplying high-temperature and high-pressure water of no less than two types with different temperature and pressure conditions into the reaction system. The pressure inside the reactor can be controlled with a pressure, adjusting valve if a flow system is used. Furthermore, the pressure can be also controlled by introducing nitrogen or other gas. The pressure used typically should be no less than the pressure generated at the temperature used.

The object of the present invention can basically be attained under high-temperature and high-pressure water conditions with a temperature of no less than 250° C. and a pressure of no less than 15 MPa. The object of the present invention can be attained more advantageously under high-temperature and high-pressure water conditions with a temperature of no less than 300° C. and a pressure of no less than 15 MPa. The object of the present invention can be attained even more advantageously by selecting high-temperature and high-pressure water conditions with a temperature within a range of no less than 300° C. and a pressure within a range of 20 to 50 MPa. Furthermore, the object of the present invention can be attained most advantageously by selecting high-temperature and high-pressure water conditions with a temperature of no less than 330° C. and a pressure within a range of 20 to 50 MPa. Optimum temperature conditions vary depending on processing time or pressure, but generally a temperature range from 250° C. to 450° C. can advantageously be selected. A temperature range from 330° C. to 420° C. can be selected more advantageously. A temperature range from 350° C. to 400° C. can be selected most advantageously. The appropriate temperature and pressure conditions can be employed according to the processing quantity or reaction apparatus. In accordance with the present invention, the reaction sufficiently proceeds at a temperature within a range of 350 to 400° C. and it is found that the reaction tends to accelerate as the pressure rises.

For example, a high-temperature and high-pressure reactor can be used as the above-mentioned reactor. However, such a reactor is not limiting and no restriction is placed on the type of the reactor, provided that the fluid reaction system can be set under high-temperature and high-pressure conditions. A flow-type high-temperature and high-pressure reactor used in the Examples is an example of the preferred reactor.

In accordance with the present invention, an organic solvent at room temperature having an oxime dissolved therein is introduced into flowing high-temperature and high-pressure water. Therefore, the temperature drops after mixing. The degree of temperature decrease changes depending on the initial temperature of carrier water, reaction pressure, flow velocity of carrier water, inlet flow velocity of the oxime-containing solvent, quantity of introduced oxime, type of the reactor, reactor capacity, and the like. In accordance with the present invention, a set reaction temperature can be attained within a short time of no more than 3 seconds, for example, by raising the temperature of carrier fluid in advance to above a set reaction temperature and mixing with a substrate solution at a temperature of no higher than 100° C. The set temperature of carrier water apparently varies depending on the size, capacity and shape of reaction vessel, type, temperature, and pressure of carrier water and substrate solution, the flow velocity ratio thereof, and the like. However, typically the temperature of carrier water can be set higher than the set reaction temperature by 5 to 400° C., and it is desired that the reaction be conducted at a set temperature of carrier water which is higher than the set reaction temperature by a temperature preferably within a range of 5 to 300° C., more preferably 5 to 250° C., and most preferably 5 to 200° C.

In accordance with the present invention, setting the mixing ratio of carrier water and substrate solution is important for determining the reaction temperature. Usually, the mixing ratio can be controlled by controlling the feed rate of carrier water and substrate solution. If the flow velocity of carrier water is taken as 1, a value within a range of 0.0001 to 1 can be appropriately selected as the flow velocity of substrate solution. However, it is desired that this value be preferably selected from a range of 0.001 to 1, more preferably from a range of 0.005 to 1, and most preferably from a range of 0.01 to 1.

Even if the same flow velocity is used, the employed flow rate fluctuates depending on the size, cross section area, length, and the like of the reaction container. Therefore, a linear speed can be used instead of flow velocity. In accordance with the present invention, a flow rate with a linear speed of $10^{-3}$ to $10^3$ m/sec can usually be used as the flow rate of carrier water or substrate solution. It is desired that preferably a flow rate with a linear speed of $10^{-2}$ to $10^3$ m/sec, more preferably a flow rate with a linear speed of $10^{-2}$ to $10^2$ m/sec, even more preferably a flow rate with a linear speed of $10^{-1}$ to $10^2$ m/sec, and most preferably a flow rate with a linear speed of $10^{-1}$ to $10^1$ m/sec be used. Further, the mixing ratio of carrier water and substrate solution can be also represented by the ratio of linear speed values. When the linear speed of carrier fluid is takes as 1, a value within a range of 0.0001 to 1 can usually be appropriately selected as the linear speed of substrate solution. However, it is desired that a value within a range of preferably 0.001 to 1, more preferably, 0.005 to 1, and most preferably, 0.01 to 1 be selected.

In accordance with the present invention, the prescribed high-temperature and high-pressure fluid can be produced by preferably using, for example, acetonitrile, dimethyl sulfoxide, ethyl alcohol, methyl alcohol, 1,4-dioxane, and the like as the organic solvent used for dissolving the oxime. However, the solvents that can be used in accordance with the present invention are not limited to the above-mentioned solvents and the below-described solvents can be used in appropriate combinations of one or more thereof. Thus, examples of appropriate solvents include nitriles containing cyano group, for example, benzonitrile and the like, urea or amides containing amido group, for example, formamide, N-methyl formamide, N,N'-dimethyl acetamide, pyrrolidone, N-methyl pyrrolidone, N,N'-dimethyl ethylene urea, N,N'-dimethyl propylene urea, N,N-dimethyl formamide, tetrahydrofuran, and the like, amines containing amino groups, for example, quinoline, triethylamine, tributylamine, and the like, sulfides, sulfoxides, for example, sulfolan and the like, phosphoric acid esters, such as hexamethylenephosphoric acid and the like, alcohols having hydroxy group, for example, propanol, isopropanol, butanol, pentanol, cyclopentanol, hexanol, cyclohexanol, heptanol, cycloheptanol, octanol, cyclooctanol, nonanol, decanol, dodecanol, tridecanol, tetradecanol, heptadecanol, cycloheptanol, methoxyethanol, chloroethanol, trifluoroethanol, hexafluoropropanol, phenol, benzyl alcohol, ethylene glycol, triethylene glycol, and the like, carboxylic acids or esters which are derivatives of carboxylic acids, carbonic acid or carbonic acid esters, such as ethyl acetate, methyl acetate, formic acid, acetic acid, dimethyl carbonate, diethyl carbonate, propylene carbonate, aldehydes or ketones having carbonyl group, for example, acetone, 2-butanone, 3-pentanone, diethyl ketone, methyl ethyl ketone, methyl propyl ketone, butyl methyl ketone, cyclohexanone, acetophenone, and the like, ethers, for example, diglyme, diethyl ether, anisole, and the like, hydrocarbons with low polarity, for example, pentane, hexane, heptane, cyclohexane, decaline, benzene, toluene, xylene, perfluorobenzene, fluorobenzene, hexafluorobenzene, and the like, and imidazole derivative salts which are ionic fluids or halogenated hydrocarbons such as methylene chloride and the like. Selecting an organic solvent of at least one type selected from the group of those organic solvents, or appropriately mixing such organic solvents makes it possible to use them as an organic solvent for dissolving oximes or as an organic solvent having a function of enhancing the Beckman rearrangement reaction of oximes.

A major feature of the present invention is that the oxime temperature increase time is reduced to a short time of no more than 3 seconds by directly introducing an organic solvent having the oxime dissolved therein into a high-temperature and high-pressure water with a temperature by about 5 to 300° C. higher than the set temperature, as has been described hereinabove. As a result, the hydrolysis reaction of oxime can be suppressed and, therefore, selectivity and yield of lactam can be increased. It is desired that preferably, the oxime temperature increase time be no more than 1 second, more preferably no more than 0.5 second, and most preferably no more than 0.3 second.

In particular, when carrier water in a supercritical state is used, the viscosity of fluid decreases and diffusion coefficient thereof increases with respect to those of liquid carrier water, which apparently results in a rapid increase in mixing speed. Furthermore, in high-temperature and high-pressure water under subcritical conditions close to a supercritical point, dielectric constant is known to decrease and solubility of organic matter is known to increase dramatically. Similarly, solubility of oxime or organic solvent also increases apparently providing advantageous conditions for rearrangement reaction.

The reaction conditions change depending on the type and concentration of the oxime which is used, volume of the reaction tube, high-temperature and high-pressure water conditions, reaction time, and the like. In accordance with the present invention, the oximes dissolved in an organic solvent used for the reaction are not limited to one type and the reaction also advantageously proceeds when a mixture of two or more of oximes is used.

The concentration of oxime introduced into the reactor can be controlled by controlling the flow velocity of high-temperature and high-pressure water used as a flow-type carrier water and the inlet flow velocity of the organic solvent containing the oxime which is a reaction substrate. Usually, the concentration of oxime introduced into the reactor can be selected within a concentration range from 1 mM to 10 M. The appropriate concentration value can advantageously be selected between 2 mM and 5 M, and most advantageously between 2 mM and 2 M. The present invention is, however, not limited to those concentration values.

In accordance with the present invention, the reaction yield of lactam can be controlled by adjusting the temperature and pressure in the reaction system, inner diameter of the reactor, volume of the reactor, flow velocity, linear speed, type of organic solvent, concentration of the reaction substrate, reaction time, and the like according to the type of oxime.

In the reaction system in accordance with the present invention, an organic solvent having dissolved therein an oxime, which is the above-mentioned reaction substrate, may be present in high-temperature and high-pressure water at a temperature of no less than 250° C. and a pressure of no less than 15 MPa. In this case, the reaction proceeds even if, for example, water-soluble catalysts such as metal ions, acids, bases, and the like, or solid catalysts such as metal-supported catalysts, solid acids, solid bases, and the like, or enzymes are not intentionally added. The most important specific feature of the present invention is basically that a lactam is synthesized from an oxime in the presence of an organic solvent having the above-described reaction substrate dissolved therein in high-temperature and high-pressure water, but if necessary, water-soluble catalysts such as metal ions, acids, bases, and the like, or solid catalysts such as metal-supported catalysts, solid acids, solid bases, and the like, or enzymes may be added without producing even slightest effect on the reaction.

In accordance with the present invention, a lactam can usually be synthesized from an oxime within a short reaction time from 0.001 second to 60 seconds in the above-described reaction system. When a flow reactor is used, the reaction time can be controlled by controlling the reaction time, reaction pressure, flow velocity or linear speed of high-temperature and high-pressure water, inlet flow velocity or linear speed of reaction substrate, shape of the reactor, inner diameter of the reaction, length of flow channel in the reactor, and the like. More preferably, a value within a range from 0.01 second to 30 seconds can be selected, even more preferably, a value within a range from 0.01 second to 20 seconds can be selected, still more preferably, a value within a range from 0.05 second to 10 seconds can be selected, and most preferably, a value within a range from 0.05 second to 5 seconds can be selected as the reaction time; the present invention is, however, not limited to those values.

By using a high-performance liquid chromatography instrument combined with mass spectrometer (LC-MS device), a gas chromatograph analysis device, a nuclear magnetic resonance spectrum measurement device (NMR measurement device), or Fourier IR spectrophotometer (FTIR device), the inventors have confirmed the possibility of the rearrangement reaction from oximes into lactams proceeding within a short time (for example, a reaction time of about 1 sec) under the high-temperature and high-pressure water conditions, as shown in the below-described examples. Furthermore, types of oximes, lactams, or amino acids which are byproducts can be identified and their amounts can be quantitatively determined with good accuracy by using the LC-MS device. Moreover, types of lactams can be accurately identified by separating and purifying the continuously obtained lactams with an ion-exchange resin column, measuring the IR absorption spectrum with a FTIR measurement device and comparing the spectrum with that of a high-purity special reagent. Similarly, the type or purity of lactams can be confirmed by NMR spectral measurements. The structure of lactams can be confirmed with a gas chromatography instrument combined with mass spectrometer (GC-MS device), LS-MS device, NMR measurement device, or FTIR device.

The reaction yield of lactams formed in accordance with the present invention varies depending on the reaction conditions such as temperature, pressure, and the like, type of oxime, concentration of oxime, type of organic solvent, presence of acid additives, configuration of the reaction unit, size of the reactor, flow velocity and linear speed of carrier water, oxime inlet velocity or linear speed, reaction time, and the like. In some cases, the obtained $\epsilon$-caprolactam is recovered in a mixture with cyclohexanone oxime which is a starting material. Similarly, with the present invention, lactams and amino acids of various types can be recovered together with a starting material substrate from various oximes or mixtures thereof. However, lactams and amino acids can be purified and concentrated for each type thereof, because lactams, amino acids, and oximes which are starting materials can be separated, for example, by using a solvent extraction method or by employing a cation-exchange resin, an anion-exchange resin, or both, and then lactams and amino acids can be separated, or lactams can be separated one from another. Moreover, oximes that have been also recovered can be reused as starting materials.

Therefore, high-purity lactams and amino acids can advantageously be produced by conducting rearrangement reaction of oximes under high-temperature and high-pressure water conditions, synthesizing lactams and amino acids, and employing a solvent extraction method with respect to the obtained reaction solution, or by separating and purifying the lactams and amino acids by using ion-exchange resins.

[Function]

In accordance with the present invention, for example, $\epsilon$-caprolactam can be synthesized from cyclohexanone oxime by introducing an organic solvent having the oxime dissolved therein as a reaction substrate into a high-temperature hot water under high-temperature and high-pressure water conditions, raising the temperature of the reaction substrate within a short time, and conducting the reaction under the prescribed high-temperature and high-pressure water conditions. Furthermore, a variety of lactams corresponding to respective oximes can be continuously synthesized by continuously introducing an organic solvent having those oximes dissolved therein into flowing high-temperature and high-pressure water.

Therefore, the present invention is useful in providing a novel method for producing lactams that is a new method for continuously producing lactams which makes it possible to produce lactams continuously within a short time by adjusting reaction conditions, type of oxime serving as the reaction substrate, concentration of oxime, type of organic solvent, and the like, in the reaction system.

1 THERMOCOUPLE
2 THERMOCOUPLE
3 REACTOR
4 LIQUID PUMP
5 LIQUID PUMP
6 CARRIER WATER
7 SUBSTRATE SOLUTION
8 HEATER
9 COOLING UNIT
10 PRESSURE ADJUSTING VALVE
11 SAMPLE RECOVERY VESSEL

EXAMPLES

The present invention will be described hereinbelow in greater detail based on embodiments thereof. The present invention is, however, not limited to the embodiments.

Example 1

Figure 1:
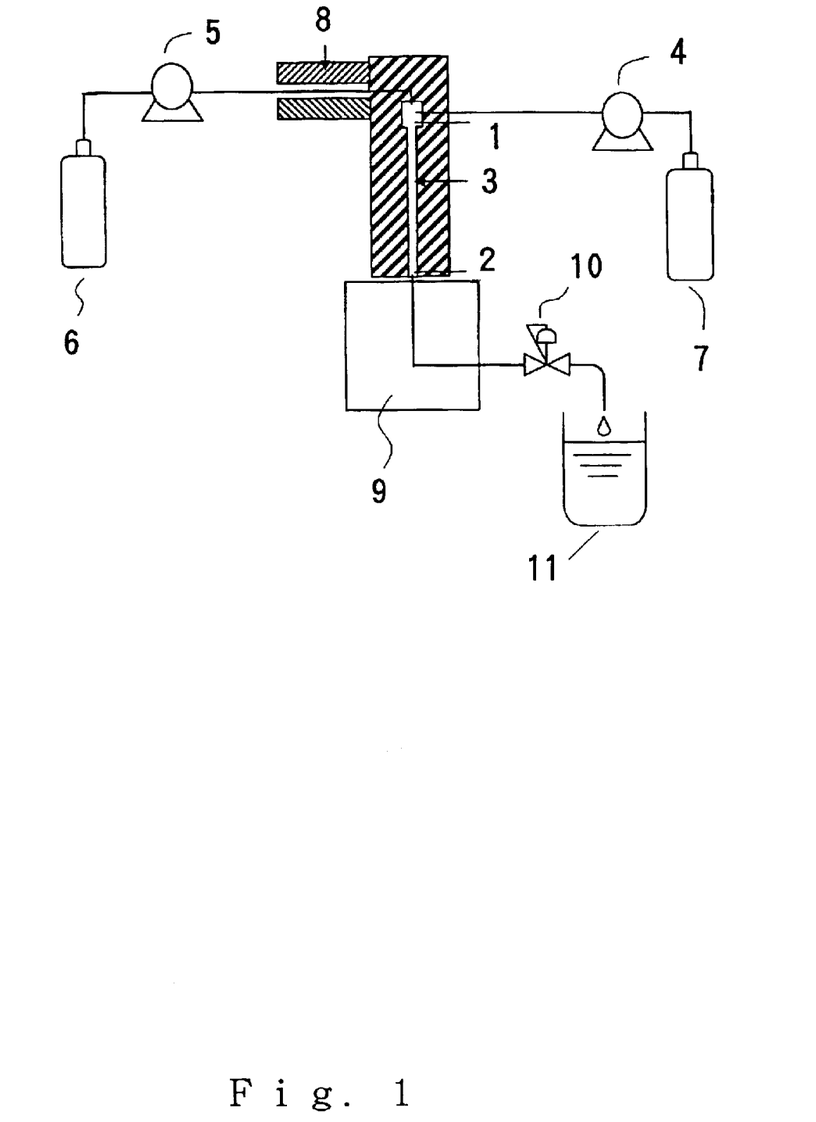
FIG. 1 illustrates schematically a flow-type high-temperature and high-pressure reactor equipped with two water pumps, this reactor being used in the embodiments.

Continuous production of $\epsilon$-caprolactam by the rearrangement reaction was attempted by employing a continuous high-temperature and high-pressure reactor shown in FIG. 1 and using a cyclohexanone oxime reagent (produced by Aldrich Chemical Company, Inc., purity 97%) under conditions of a high-pressure and high-temperature acetonitrile—water mixture at a temperature of 375° C. and under pressure of 40 MPa.

The material of a reactor 3 was HASTELLOY C-276, the inner diameter of the reactor was 0.325 mm and the reactor length was 120 cm. Therefore, the calculated capacity of the reactor was 0.0995 cm³. Each introduced preparation liquid was pumped in with high-pressure pumps 4, 5. Distilled water from which dissolved oxygen was purged out by bubbling with nitrogen was heated to prepare carrier water 6 at 470° C. and 40 MPa and the water was passed at a flow velocity of 3.3 mL/min. The linear speed was $6.63 \times 10^{-1}$ m/sec. A substrate solution containing 21.9 mM cyclohexanone oxime was prepared by using acetonitrile solution similarly subjected to deoxidation treatment. The substrate solution 7 at room temperature and 40 MPa was introduced into and mixed with the carrier water in an inlet opening of the reactor at a flow velocity of 1.8 mL/min (linear speed $3.62 \times 10^{-1}$ m/sec). The reaction temperature of the mixed solution measured with a thermocouple disposed at a distance of 1 cm from the inlet opening of the reactor was 375° C. and matched the temperature measured with a thermocouple in the outlet opening of the reactor, thereby suggesting that the temperature inside the reactor was constant and that the carrier water and substrate solution were mixed homogeneously. The calculated flow velocity of high-temperature and high-pressure acetonitrile—water mixture was 5.1 mL/min and the linear speed thereof was $1.02 \times 10^0$ m/sec. The water mixture had a density corresponding to the mixing ratio of acetonitrile and water. Under an assumption that acetonitrile behaves identically to water at a high temperature and under a high pressure, the density of the acetonitrile—water mixture at a temperature of 375° C. and under a pressure of 40 MPa was 0.5633 g/cm³. The substrate concentration after mixing in acetonitrile—water mixture was 7.7 mM. The reaction time was 0.659 sec. Therefore, mixing was apparently completed within a short time of no more than 0.006 sec. Examination of the acetonitrile—water mixture solution recovered after the reaction with the high-performance liquid chromatography instrument combined with mass spectrometer and the gas chromatograph analysis device confirmed the formation of ∈-caprolactam as a main product and 6-aminohexanoic acid as a byproduct. In addition, only unreacted cyclohexanone oxime was detected and cyclohexanone that was a hydrolyzate of the starting material practically was not detected. The molar concentration of ∈-caprolactam was 6.2 mM and the reaction yield thereof was 80.5%. On the other hand, the content of 6-aminohexanoic acid was 0.4 mM and the reaction yield thereof was 5.2%.

Example 2

Continuous production of ∈-caprolactam by the rearrangement reaction of cyclohexanone oxime was attempted by using 10 vol. % acetonitrile-containing aqueous solution as a substrate solution and conducting the reaction by the operations identical to those of Example 1. The process was implemented under the following reaction conditions.
Reaction Conditions Temperature and pressure of carrier water: 464° C. and 40 MPa.

Flow velocity and linear speed of carrier water: 3.5 mL/min and $7.03 \times 10^{-1}$ m/sec.

Temperature and pressure of 21.7 mM substrate solution: room temperature and 40 MPa.

Flow velocity and linear speed of 21.7 mM substrate solution: 1.5 mL/min and $3.01 \times 10^{-1}$ m/sec.

Temperature of reaction high-temperature and high-pressure acetonitrile—water mixture: 375° C.

Pressure of reaction high-temperature and high-pressure acetonitrile—water mixture: 40 MPa.

Density of reaction high-temperature and high-pressure acetonitrile—water mixture: 0.6063 g/cm³.

Flow velocity and linear speed of reaction high-temperature and high-pressure acetonitrile—water mixture: 5.0 mL/min and $1.00 \times 10^0$ m/sec.

The substrate concentration of cyclohexanone oxime after mixing was 6.5 mM. The reaction time was 0.724 second and because the temperature inside the reactor was constant, it could be inferred that the components were mixed within a short time of no more than 0.007 second. Examination of the aqueous solution with the high-performance liquid chromatography instrument combined with mass spectrometer and the gas chromatograph analysis device after the reaction confirmed the formation of ∈-caprolactam as a main product and 6-aminohexanoic acid as a byproduct. Unreacted cyclohexanone oxime was also detected. The molar concentration of ∈-caprolactam was 5.0 mM and the reaction yield thereof was 76.9%. The content of 6-aminohexanoic acid was 0.3 mM and the reaction yield thereof was 4.6%.

Comparative Example 1

Continuous production of ∈-caprolactam by the rearrangement reaction of cyclohexanone oxime was attempted by dissolving cyclohexanone oxime in distilled water to prepare a substrate solution and conducting the reaction by the operations identical to those of Example 1. The process was implemented under the following reaction conditions.
Reaction Conditions Temperature and pressure of carrier water: 475° C. and 40 MPa.

Flow velocity and linear speed of carrier water: 3.9 mL/min and $7.84 \times 10^{-1}$ m/sec.

Temperature and pressure of 21.9 mM substrate solution room temperature and 40 MPa.

Flow velocity and linear speed of 21.9 mM substrate solution: 1.1 mL/min and $2.21 \times 10^{-1}$ m/sec.

Temperature of reaction high-temperature and high-pressure water: 375° C.

Pressure of reaction high-temperature and high-pressure water: 40 MPa.

Density of reaction high-temperature and high-pressure water: 0.6096 g/cm³.

Flow velocity and linear speed of reaction high-temperature and high-pressure water: 5.0 mL/min and $1.00 \times 10^0$ m/sec.

The substrate concentration of cyclohexanone oxime after mixing was 4.8 mM. The reaction time was 0.728 second and because the temperature inside the reactor was constant, the carrier water and substrate solution were apparently mixed within a short time of no more than 0.007 sec. Examination of the aqueous solution with the high-performance liquid chromatography instrument combined with mass spectrometer and the gas chromatograph analysis device after the reaction confirmed the formation of ∈-caprolactam as a main product and 6-aminohexanoic acid as a byproduct. Unreacted cyclohexanone oxime was also detected. The molar concentration of ∈-caprolactam was 2.8 mM and the reaction yield thereof was 58.3%. The molar concentration of 6-aminohexanoic acid was 0.06 mM and the reaction yield thereof was 1.3%.

Example 3

Continuous production of ∈-caprolactam by the rearrangement reaction of cyclohexanone oxime was attempted by dissolving cyclohexanone oxime and sulfuric acid in acetonitrile solution to prepare a substrate solution and conducting the reaction by the operations identical to those of Example 1. The concentration of sulfuric acid in the substrate solution was 5 mM. The process was implemented under the following reaction conditions.

Reaction Conditions

Temperature and pressure of carrier water: 430° C. and 40 MPa.

Flow velocity and linear speed of carrier water: 2.9 mL/min and $5.83 \times 10^{-1}$ m/sec.

Temperature and pressure of 0.3507 M substrate solution room temperature and 40 MPa.

Flow velocity and linear speed of 0.3507 M substrate solution: 2.1 mL/min and $4.22 \times 10^{-1}$ m/sec.

Temperature of reaction high-temperature and high-pressure acetonitrile—water mixture: 350° C.

Pressure of reaction high-temperature and high-pressure acetonitrile—water mixture: 40 MPa.

Density of reaction high-temperature and high-pressure acetonitrile—water mixture: 0.6108 g/cm$^3$.

Flow velocity and linear speed of reaction high-temperature and high-pressure acetonitrile—water mixture: 5.0 mL/min and $1.00 \times 10^0$ m/sec.

The substrate concentration of cyclohexanone oxime after mixing was 147.3 mM and sulfuric acid concentration was 2.1 mM. The reaction time was 0.729 second and because the temperature inside the reactor was constant, the carrier water and substrate solution were apparently mixed within a short time of no more than 0.007 sec. Examination of the acetonitrile—water mixture solution with the high-performance liquid chromatography instrument combined with mass spectrometer and the gas chromatograph analysis device after the reaction confirmed the formation of ε-caprolactam as a main product and 6-aminohexanoic acid as a byproduct. Cyclohexanone oxime that was a starting material and cyclohexanone that was a hydrolyzate of the starting material practically were not detected. The molar concentration of ε-caprolactam was 130.0 mM and the reaction yield thereof was 88.3%. The molar concentration of 6-aminohexanoic acid was 1.73 mM and the reaction yield thereof was 11.7%.

Comparative Example 2

Continuous production of ε-caprolactam by the rearrangement reaction of cyclohexanone oxime was attempted by dissolving cyclohexanone oxime in distilled water to prepare a substrate solution and conducting the reaction by the operations identical to those of Example 1. The process was implemented under the following reaction conditions.

Reaction Conditions

Temperature and pressure of carrier water: 445° C. and 40 MPa.

Flow velocity and linear speed of carrier water: 3.9 mL/min and $7.84 \times 10^{-1}$ m/sec.

Temperature and pressure of 21.9 mM substrate solution room temperature and 40 MPa.

Flow velocity and linear speed of 21.9 mM substrate solution: 1.1 mL/min and $2.21 \times 10^1$ m/sec.

Temperature of reaction high-temperature and high-pressure water: 350° C.

Pressure of reaction high-temperature and high-pressure water: 40 MPa.

Density of reaction high-temperature and high-pressure water: 0.6721 g/cm$^3$.

Flow velocity and linear speed of reaction high-temperature and high-pressure water: 5.0 mL/min and $1.0 \times 10^0$ m/sec.

The substrate concentration of cyclohexanone oxime after mixing was 4.8 mM. The reaction time was 0.802 second and because the temperature inside the reactor was constant, the carrier water and substrate solution were apparently mixed within a short time of no more than 0.007 sec. Examination of the aqueous solution with the high-performance liquid chromatography instrument combined with mass spectrometer and the gas chromatograph analysis device after the reaction confirmed the formation of ε-caprolactam as a main product and 6-aminohexanoic acid as a byproduct. Unreacted cyclohexanone oxime was also detected. The molar concentration of ε-caprolactam was 1.8 mM and the reaction yield thereof was 37.5%. The molar concentration of 6-aminohexanoic acid was 0.02 mM and the reaction yield thereof was 0.4%.

Example 4

Continuous production of ε-caprolactam by the rearrangement reaction of cyclohexanone oxime was attempted by conducting the reaction by the operations identical to those of Example 3. However, 5 mM nitric acid was used as the acid present in the substrate solution and the process was implemented under the following reaction conditions.

Reaction Conditions

Temperature and pressure of carrier water: 490° C. and 40 MPa.

Flow velocity and linear speed of carrier water: 3.1 mL/min and $6.23 \times 10^{-1}$ m/sec.

Temperature and pressure of 0.1750 M substrate solution: room temperature and 40 MPa.

Flow velocity and linear speed of 0.1750 M substrate solution: 1.9 mL/min and $3.82 \times 10^{-1}$ m/sec.

Temperature of reaction high-temperature and high-pressure acetonitrile—water mixture: 375° C.

Pressure of reaction high-temperature and high-pressure acetonitrile—water mixture: 40 MPa.

Density of reaction high-temperature and high-pressure acetonitrile—water mixture: 0.5593 g/cm$^3$.

Flow velocity and linear speed of reaction high-temperature and high-pressure acetonitrile—water mixture: 5.0 mL/min and $1.00 \times 10^0$ m/sec.

The substrate concentration of cyclohexanone oxime after mixing was 66.5 mM and the concentration of nitric acid was 1.9 mM. The reaction time was 0.668 second and because the temperature inside the reactor was constant, the components were apparently mixed homogeneously within a short time of no more than 0.006 second. Examination of the acetonitrile mixed aqueous solution with the high-performance liquid chromatography instrument combined with mass spectrometer and the gas chromatograph analysis device after the reaction confirmed the formation of ε-caprolactam as a main product and 6-aminohexanoic acid as a byproduct. Cyclohexanone oxime that was a starting material and cyclohexanone that was a hydrolyzate of the starting material practically were not detected. The molar concentration of ε-caprolactam was 59.2 mM and the reaction yield thereof was 89.0%. On the other hand, the content of 6-aminohexanoic acid was 7.3 mM and the reaction yield thereof was 11.0%.

Example 5

Continuous production of ε-caprolactam by the rearrangement reaction of cyclohexanone oxime was attempted by using 10 vol. % acetonitrile-containing aqueous solution as a substrate solution and conducting the reaction by the operations identical to those of Example 3. However, 5 mM hydrochloric acid was used as the acid present in the substrate solution and the process was implemented under the following reaction conditions.

Reaction Conditions

Temperature and pressure of carrier water: 480° C. and 40 MPa.

Flow velocity and linear speed of carrier water: 3.6 mL/min and $7.23 \times 10^{-1}$ m/sec.

Temperature and pressure of 0.1782 M substrate solution room temperature and 40 MPa.

Flow velocity and linear speed of 0.1782 M substrate solution: 1.4 mL/min and $2.81 \times 10^{-1}$ m/sec.

Temperature of reaction high-temperature and high-pressure acetonitrile—water mixture: 380° C.

Pressure of reaction high-temperature and high-pressure acetonitrile—water mixture: 40 MPa.

Density of reaction high-temperature and high-pressure acetonitrile—water mixture: 0.5912 g/cm$^3$.

Flow velocity and linear speed of reaction high-temperature and high-pressure acetonitrile—water mixture: 5.0 mL/min and $1.00 \times 10^0$ m/sec.

The substrate concentration of cyclohexanone oxime after mixing was 49.9 mM and the concentration of hydrochloric acid was 1.4 mM. The reaction time was 0.706 second and because the temperature inside the reactor was constant, the components were apparently mixed homogeneously within a short time of no more than 0.006 second. Examination of the acetonitrile—water mixture solution with the high-performance liquid chromatography instrument combined with mass spectrometer and the gas chromatograph analysis device after the reaction confirmed the formation of ε-caprolactam as a main product and 6-aminohexanoic acid as a byproduct. Cyclohexanone oxime that was a starting material and cyclohexanone that was a hydrolyzate of the starting material practically were not detected. The molar concentration of ε-caprolactam was 43.8 mM and the reaction yield thereof was 87.8%. On the other hand, the content of 6-aminohexanoic acid was 6.1 mM and the reaction yield thereof was 12.2%.

Example 6

Continuous production of ε-caprolactam by the rearrangement reaction of cyclohexanone oxime was attempted by dissolving cyclohexanone oxime in a dimethyl sulfoxide solution to prepare a substrate solution and conducting the reaction by the operations identical to those of Example 1. The process was implemented under the following reaction conditions.

Reaction Conditions

Temperature and pressure of carrier water: 420° C. and 30 MPa.

Flow velocity and linear speed of carrier water: 3.8 mL/min and $7.63 \times 10^{-1}$ m/sec.

Temperature and pressure of 0.2308 M substrate solution: room temperature and 30 MPa.

Flow velocity and linear speed of 0.2308 M substrate solution: 1.2 mL/min and $2.41 \times 10^{-1}$ m/sec.

Temperature of reaction high-temperature and high-pressure dimethyl sulfoxide—water mixture: 350° C.

Pressure of reaction high-temperature and high-pressure dimethyl sulfoxide—water mixture: 30 MPa.

Density of reaction high-temperature and high-pressure dimethyl sulfoxide—water mixture: 0.7303 g/cm$^3$.

Flow velocity and linear speed of reaction high-temperature and high-pressure dimethyl sulfoxide—water mixture: 5.0 mL/min and $1.00 \times 10^0$ m/sec.

The substrate concentration of cyclohexanone oxime after mixing was 55.4 mM. The reaction time was 0.872 second and because the temperature inside the reactor was constant, the components were apparently mixed within a short time of no more than 0.008 sec. Examination of the dimethyl sulfoxide—water mixture with the high-performance liquid chromatography instrument combined with mass spectrometer and the gas chromatograph analysis device after the reaction confirmed the formation of ε-caprolactam as a main product and 6-aminohexanoic acid as a byproduct. In addition, only unreacted cyclohexanone oxime was detected and cyclohexanone that was a hydrolyzate of the starting material practically was not detected. The molar concentration of ε-caprolactam was 50.6 mM and the reaction yield thereof was 91.3%. On the other hand, the content of 6-aminohexanoic acid was 2.6 mM and the reaction yield thereof was 4.7%.

Example 7

Continuous production of ε-caprolactam by the rearrangement reaction of cyclohexanone oxime was attempted by dissolving cyclohexanone oxime in a 1,4-dioxane solution to prepare a substrate solution and conducting the reaction by the operations identical to those of Example 1. The process was implemented under the following reaction conditions.

Reaction Conditions

Temperature and pressure of carrier water: 420° C. and 30 MPa.

Flow velocity and linear speed of carrier water: 15.6 mL/min and $3.13 \times 10^0$ m/sec.

Temperature and pressure of 0.2509 M substrate solution: 25° C. and 40 MPa.

Flow velocity and linear speed of 0.2509 M substrate solution: 4.4 mL/min and $8.84 \times 10^{-1}$ m/sec.

Temperature of reaction high-temperature and high-pressure 1,4-dioxane—water mixture: 350° C.

Pressure of reaction high-temperature and high-pressure 1,4-dioxane—water mixture: 30 MPa.

Density of reaction high-temperature and high-pressure 1,4-dioxane—water mixture: 0.6496 g/cm$^3$.

Flow velocity and linear speed of reaction high-temperature and high-pressure 1,4-dioxane—water mixture: 20.0 mL/min and $4.02 \times 10^0$ m/sec.

The substrate concentration of cyclohexanone oxime after mixing was 55.2 mM. The reaction time was 0.194 second and because the temperature inside the reactor was constant, the components were apparently mixed within a short time of no more than 0.002 sec. Examination of the 1,4-dioxane—water mixture with the high-performance liquid chromatography instrument combined with mass spectrometer and the gas chromatograph analysis device after the reaction confirmed the formation of ε-caprolactam as a main product and 6-aminohexanoic acid as a byproduct. In addition, unreacted cyclohexanone oxime was detected and cyclohexanone that was a hydrolyzate of the starting material practically was not detected. The molar concentration of ε-caprolactam was 27.9 mM and the reaction yield thereof was 50.5%. The content of 6-aminohexanoic acid was 0.9 mM and the reaction yield thereof was 1.6%.

Comparative Example 3

Continuous production of ε-caprolactam by the rearrangement reaction of cyclohexanone oxime was attempted by dissolving cyclohexanone oxime in distilled water to prepare a substrate solution and conducting the reaction by the operations identical to those of Example 1. The process was implemented under the following reaction conditions.

Reaction Conditions

Temperature and pressure of carrier water: 416° C. and 30 MPa.

Flow velocity and linear speed of carrier water: 3.9 mL/min and $7.84 \times 10^{-1}$ m/sec.

Temperature and pressure of 21.9 mM substrate solution: room temperature and 40 MPa.

Flow velocity and linear speed of 21.9 mM substrate solution: 1.2 mL/min and $2.41 \times 10^{-1}$ m/sec.

Temperature of reaction high-temperature and high-pressure water: 350° C.

Pressure of reaction high-temperature and high-pressure water: 30 MPa.

Density of reaction high-temperature and high-pressure water: 0.6443 g/cm$^3$.

Flow velocity and linear speed of reaction high-temperature and high-pressure water: 5.1 mL/min and $1.02 \times 10^0$ m/sec.

The substrate concentration of cyclohexanone oxime after mixing was 5.2 mM. The reaction time was 0.769 second and because the temperature inside the reactor was constant, the carrier water and substrate solution were apparently mixed within a short time of no more than 0.007 sec. Examination of the aqueous solution with the high-performance liquid chromatography instrument combined with mass spectrometer and the gas chromatograph analysis device after the reaction confirmed the formation of ε-caprolactam as a main product and 6-aminohexanoic acid as a byproduct. Unreacted cyclohexanone oxime was also detected. The molar concentration of ε-caprolactam was 1.7 mM and the reaction yield thereof was 32.7%. The molar concentration of 6-aminohexanoic acid was 0.01 mM and the reaction yield thereof was 0.2%.

Example 8

Continuous production of ε-caprolactam by the rearrangement reaction of cyclohexanone oxime was attempted by conducting the reaction by the operations identical to those of Example 4. However, ethyl alcohol was used as the substrate solution, 5 mM nitric acid was used as the acid in the substrate solution, and the process was implemented under the following reaction conditions.

Reaction Conditions

Temperature and pressure of carrier water: 450° C. and 30 MPa.

Flow velocity and linear speed of carrier water: 8.7 mL/min and $1.75 \times 10^0$ m/sec.

Temperature and pressure of 0.2520 M substrate solution: room temperature and 40 MPa.

Flow velocity and linear speed of 0.2520 M substrate solution: 3.4 mL/min and $6.83 \times 10^{-1}$ m/sec.

Temperature of reaction high-temperature and high-pressure ethyl alcohol—water mixture: 375° C.

Pressure of reaction high-temperature and high-pressure ethyl alcohol—water mixture: 30 MPa.

Density of reaction high-temperature and high-pressure ethyl alcohol—water mixture: 0.5250 g/cm$^3$.

Flow velocity and linear speed of reaction high-temperature and high-pressure ethyl alcohol—water mixture: 12.1 mL/min and $2.43 \times 10^0$ m/sec.

The substrate concentration of cyclohexanone oxime after mixing was 181.2 mM and the concentration of nitric acid was 3.6 mM. The reaction time was 0.259 second and because the temperature inside the reactor was constant, the components were apparently mixed homogeneously within a short time of no more than 0.003 sec. Examination of the ethyl alcohol—water mixture solution with the high-performance liquid chromatography instrument combined with mass spectrometer and the gas chromatograph analysis device after the reaction confirmed the formation of ε-caprolactam as a main product and 6-aminohexanoic acid as a byproduct. Cyclohexanone oxime that was a starting material and cyclohexanone that was a hydrolyzate practically were not detected. The molar concentration of ε-caprolactam was 175.6 mM and the reaction yield thereof was 96.9%. On the other hand, the content of 6-aminohexanoic acid was 5.6 mM and the reaction yield thereof was 3.1%.

Example 9

Continuous production of ε-caprolactam by the rearrangement reaction of cyclohexanone oxime was attempted by conducting the reaction by the operations identical to those of Example 8. However, methyl alcohol was used as the substrate solution, 5 mM nitric acid was used as the acid in the substrate solution, and the process was implemented under the following reaction conditions.

Reaction Conditions

Temperature and pressure of carrier water: 450° C. and 40 MPa.

Flow velocity and linear speed of carrier water: 9.5 mL/min and $1.91 \times 10^0$ m/sec.

Temperature and pressure of 0.2810 M substrate solution room temperature and 40 MPa.

Flow velocity and linear speed of 0.2810 M substrate solution: 2.6 mL/min and $5.22 \times 10^{-1}$ m/sec.

Temperature of reaction high-temperature and high-pressure methyl alcohol—water mixture: 375° C.

Pressure of reaction high-temperature and high-pressure methyl alcohol—water mixture: 40 MPa.

Density of reaction high-temperature and high-pressure methyl alcohol—water mixture: 0.5829 g/cm$^3$.

Flow velocity and linear speed of reaction high-temperature and high-pressure methyl alcohol—water mixture: 12.1 mL/min and $2.43 \times 10^0$ m/sec.

The substrate concentration of cyclohexanone oxime after mixing was 220.6 mM and the concentration of nitric acid was 3.9 mM. The reaction time was 0.288 second and because the temperature inside the reactor was constant, the components were apparently mixed homogeneously within a short time of no more than 0.003 sec. Examination of the methyl alcohol—water mixture solution with the high-performance liquid chromatography instrument combined with mass spectrometer and the gas chromatograph analysis device after the reaction confirmed the formation of ε-caprolactam as a main product and 6-aminohexanoic acid as a byproduct. Cyclohexanone oxime that was a starting material and cyclohexanone that was a hydrolyzate practically were not detected. The molar concentration of ε-caprolactam was 211.1 mM and the reaction yield thereof was 95.7%. On the other hand, the content of 6-aminohexanoic acid was 9.5 mM and the reaction yield thereof was 4.3%.

As described in details hereinabove, the present invention relates to a method for continuously producing lactams by which a high-concentration lactam is effectively synthesized, without causing a hydrolysis reaction, by introducing an oxime dissolved in an organic solvent into flowing high-temperature and high-pressure water, and more particularly to a continuous method for producing lactams by which lactams are selectively produced from oximes under high-temperature and high-pressure water mixture conditions. With the present invention, the following exceptional effects can be obtained: (1) the reaction can be conducted by raising temperature to the prescribed high-temperature and high-pressure conditions within a short time; (2) as a result, hydrolysis of oximes is suppressed and lactams can be synthesized by a rearrangement reaction of oximes; (3) lactams can be effectively produced from high-concentration oximes dissolved in organic solvents; (4) using organic solvents and acids makes it possible to produce lactams at a high yield; and (5) lactams can be produced within a short time by conducting the reaction with oximes at a high temperature and under a high pressure.

What is claimed is:

1. A method for producing a lactam represented by formula (1), formula (1)

where n is from 1 to 9 and $R_1$ is H or an alkyl group, comprising introducing an oxime represented by formula (2)

formula (2)

where n is from 1 to 9 and $R_1$ is H or an alkyl group, dissolved in an organic solvent and/or a mixed aqueous solution of an organic solvent of nitrile, sulfoxide, alcohol or ether as a substrate fluid into high-temperature and high-pressure water of no less than 250° C. and no less than 15 MPa of a carrier fluid, thereby raising the temperature of the reaction solution within a short time to prescribed high-temperature and high-pressure conditions to synthesize a lactam from the oxime in the conditions.

2. The method for producing a lactam according to claim 1, wherein the oxime dissolved in an organic solvent and/or a mixed aqueous solution of an organic solvent is introduced into continuously flowing high-temperature and high-pressure water.

3. The method for producing a lactam according to claim 1 or 2, wherein the organic solvent is composed of at least one of acetonitrile, dimethyl sulfoxide, ethyl alcohol, methyl alcohol, and 1,4-dioxane.

4. The method for producing a lactam according to claim 1, wherein the prescribed high-temperature and high-pressure conditions are a temperature range from 330° C. to 420° C. and a pressure range from 20 MPa to 50 MPa.

5. The method for producing a lactam according to claim 1 or 2, wherein a substrate solution in which an oxime and an acid have been dissolved separately or simultaneously is introduced into continuously flowing high-temperature and high-pressure water.

6. The method for producing a lactam according to claim 1, wherein the lactam is synthesized by raising the temperature of the reaction solution within a short time of no more than 3 seconds to prescribed high-temperature and high-pressure conditions.

7. The method for producing a lactam according to claim 1, wherein the linear speed of the carrier fluid and/or substrate high-pressure fluid is $10^{-3}$ to $10^3$ m/sec.

8. The method for producing a lactam according to claim 1, wherein a value of the linear speed of the substrate high-pressure fluid containing reactants is within a range of 0.0001 to 1, where the linear speed of the carrier fluid is taken as 1.

9. The method for producing a lactam according to claim 1, wherein the oxime is cyclohexanone oxime.

* * * * *